United States Patent [19]
Pendergast et al.

[11] Patent Number: 5,837,861
[45] Date of Patent: Nov. 17, 1998

[54] DINUCLEOTIDES AND THEIR USE AS MODULATORS OF MUCOCILIARY CLEARANCE AND CILIARY BEAT FREQUENCY

[75] Inventors: William Pendergast, Durham; Benjamin R. Yerxa, Raleigh; Janet L. Rideout, Raleigh; Suhaib M. Siddiqi, Raleigh, all of N.C.

[73] Assignee: Inspire Pharmaceuticals, Inc., Durham, N.C.

[21] Appl. No.: 798,508

[22] Filed: Feb. 10, 1997

[51] Int. Cl.⁶ .......................... C07H 21/00; C07H 21/02
[52] U.S. Cl. ........................................ 536/25.6; 536/26.23
[58] Field of Search ................................ 536/26.23, 25.6

[56] References Cited

PUBLICATIONS

A. Moss and V. Parsons, *National Center for Health Statistics*, 1986:66–7, DHHS Publication No. (PHS) 86–1588 (1985).
J. Klein, *Clin. Infect. Dis.* 19, 823–33 (1994).
M. Lethem, et al., *Am. J. Respir. Cell Mol. Biol.* 9, 315–22 (1993).
D. Drutz, et al. *Drug Dev. Res.* 37(3), 185 (1996).
S. Mason, et al., *Br. J. Pharamcol.* 103, 1649–56 (1991).
L. Gobran, *Am. J. Physiol.* 267, L625–L633 (1994).
M. Knowles, et al., *N. Engl. J. Med.* 325, 533–38 (1991).
H. Brown, et al., *Mol. Pharmocol.* 40, 648–55 (1991).
K. Olivier, et al., *Am. J. Respr. Crit. Care Med.* 154, 217–23 (1996).
P. Noone, et al., *Am. J. Respir. Crit. Care Med.* 153, A530 (1996).
E. Lazarowski, E., et al., *Brit. J. Pharm.*, 116, 1619–27 (1995).
C. McKenna, et al., *J. Org. Chem.* 46, 4574–76 (1980).
D. Burton, et al., *J. Fluorine Chem.* 15, 263–266 (1980.
M.A.G. Sillero, et al., *Eur. J. Biochem.*, 76, 331 (1977).
C.G. Vallejo, et al., *Biochem. Biophy. Acta*, 483, 304 (1976).
H. Coste, et al., *J. Biol. Chem.*, 262, 12096 (1987).
K.E. Ng, et al., *Nucleic Acids Res.*, 15, 3573 (1987).
J. Stepinski, et al., *Nucleosides & Nucleotides*, 14, 717 (1995).
A. Zatorski, et al., *J. Med. Chem.*, 39, 2422 (1996).
P. Rotilan, et al., *FEBS*, 280, 371 (1991).
P.C. Zamecnik, et al., *Proc. Natl. Acad. Sci.*, 89, 2370 (1992).
J. Walker, et al., *Biochemistry*, 32, 14009 (1993).
R.H. Hiderman, et al., *J. Biol. Chem.*, 266, 6915 (1991).
J. Luthje, et al., *Eur. J. Biochem.*, 173, 241 (1988).
R.H. Silverman, et al., *Microbiological Rev.*, 43, 27 (1979).
C.D. Lobaton, et al., *Eur. J. Biochem.*, 50, 495 (1975).
G. Lowe, et al., *Nucleosides & Nucleotides*, 10, 181 (1991).
G.M. Blackburn, et al., *Nuclesides & Nucleotides*, 10, 549 (1991).
J.C. Baker, et al., *Mutation Res.*, 208, 87 (1988).
G. Klein, et al., *Biochemistry*, 27, 1897 (1988).
E. Castro, et al., *Br. J. Pharmacol.*, 100, 360 (1990).

D.R. Elmaleh, et al., *Proc. Natl. Acad. Sci.*, 81, 918 (1984).
R. Bone, et al., *J. Biol. Chem.*, 261, 16410 (1986).
U. Pohl, et al. *Fed. Amer. Soc. Exper. Bio.*, Abstr. Part I, No. 1878 (1991).
M.T. Miras–Portugal., et al., *Ann. NY Acad. Sci.*, 603, 523 (1990).
A. Guranowski, et al., *Biochemistry* 27, 2959 (1988).
F. Grummt, et al., *Plant Mol. Bio.*, 2, 41 (1983).
A.G. McLennan, et al., *Nucleic Acid Res.*, 12, 1609 (1984).
P. Zamecnik, et al., *Analytical Biochem.*, 134, 1 (1983).

(List continued on next page.)

*Primary Examiner*—Gary L. Kunz
*Attorney, Agent, or Firm*—Albert P. Halluin; John A. Bendrick; Howrey & Simon

[57] ABSTRACT

The present invention encompasses structures of the formula

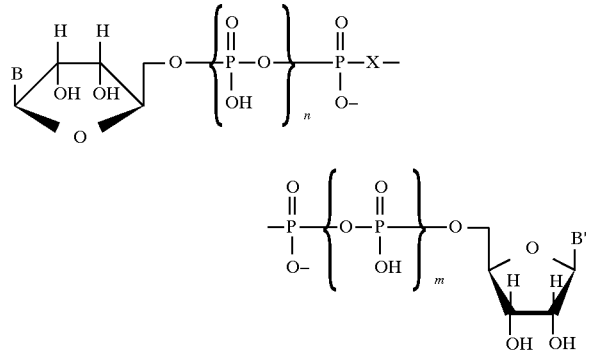

wherein:

X is oxygen, methylene, or difluoromethylene;

n=0 or 1;

m=0 or 1;

n+m=0, 1 or 2; and

B and B' are each independently a purine residue or a pyrimidine residue linked through the 9- or 1-position, respectively, provided that compounds disclosed in Table I are excluded. In the instance where B and B' are uracil, attached at the N–1 position to the ribosyl moiety, then the total of m+n may equal 3 or 4 when X is oxygen.

The compounds of the present invention are highly selective agonists of the $P2Y_2$ purinergic receptor, thus, they are useful in the treatment of chronic obstructive pulmonary diseases such as chronic bronchitis, PCD, cystic fibrosis, as well as prevention of pneumonia due to immobility. Furthermore, because of their general ability to clear retained mucus secretions and stimulate ciliary beat frequency, the compounds of the present invention are also useful in the treatment of sinusitis and otitis media.

9 Claims, No Drawings

OTHER PUBLICATIONS

E. Rapaport, et al., *Proc. Natl. Acad. Sci.,* 78, 838 (1981).
T. Kimura, et al., *Biol. Pharm. Bull.,* 18, 1556 (1995).
E. Schulze–Lohoff, et al., *Hypertension,* 26, 899 (1995).
B.K. Kim, et al., *Proc. Natl. Acad. Sci.,* 89, 11056 (1992).
H. Morii, et al., *Eur. J. Biochem.,* 205, 969 (1992).
E. Castro, et al., *Pflugers Arch.,* 426, 524 (1994).
H. Schluter, et al., *Nature,* 367, 186 (1994).
E. Castro, et al., *Br. J. Pharmacol.,* 106, 833 (1992).
T. Casillas, et al., *Biochemistry,* 32, 14203 (1993).
J. Pintor, et al., *J. Neurochem.,* 64, 670 (1995).
E. Castro, et al., *J. Biol. Chem.,* 270, 5098 (1995).
V.A. Panchenko, et al., *Neuroscience,* 70, 353 (1996).
J. Pintor, et al., *Br. J. Pharmacol.* 115, 895 (1995).
A. Kanavarioti, et al., *Tett. Lett.,* 32, 6065 (1991).

DINUCLEOTIDES AND THEIR USE AS MODULATORS OF MUCOCILIARY CLEARANCE AND CILIARY BEAT FREQUENCY

INTRODUCTION

1. Technical Field

This invention relates to certain dinucleotides which increase the hydration of retained mucus secretions, stimulate the production of mucins and increase ciliary beat frequency to increase clearance of retained secretions.

2. Background of the Invention

Chronic obstructive pulmonary disease (COPD) affects 15 million patients in the U.S. and is the sixth leading cause of death. It is characterized by the retention of mucus secretions in the lungs. Many patients diagnosed with COPD have a disorder called chronic bronchitis (CB), and 600,000 patients are hospitalized each year due to an acute exacerbation of CB. Cystic fibrosis and Primary Ciliary Dyskinesia (PCD) are other examples of lung disorders which assume a clinical profile similar to COPD. Ciliary dyskinesia, whether primary or secondary, results in retained secretions that can only be cleared by coughing.

Another disease state characterized by the accumulation of retained mucous secretions is sinusitis. Sinusitis is an inflammation of the paranasal sinuses typically associated with an upper respiratory infection. It is this country's most common health-care complaint, affecting an estimated 31 million people. (A. Moss and V. Parsons, National Center for Health Statistics, 1986: 66–7, DHHS Publication No. (PHS) 86-1588 (1985)).

Otitis media (OM) is a viral or bacterial infection of the middle ear which primarily afflicts children under the age of three. It is usually precipitated by an upper respiratory infection which spreads into the middle ear via the nasopharynx and eustachian tube. Approximately 25–50 million office visits are made each year for diagnosis and treatment of OM. By age three, about 75% of children will have had at least one episode of acute OM (J. Klein, Clin. Infect. Dis. 19, 823–33 (1994)). Following appropriate treatment with antibiotics, accumulated fluid in the middle ear remains, causing hearing impairment and potential language and cognitive development delays. Enhanced ability to clear secretions in the middle ear would reduce or eliminate significant sequelae of otitis media.

An additional disorder resulting from retained secretions is pneumonia. Patients who are immobilized for a variety of reasons are at high risk for developing pneumonia. Despite extra vigilance and numerous interventions, pneumonia develops in over 400,000 patients per year, with significant morbidity and mortality.

Mucous secretions are normally removed via the mucociliary clearance (MCC) system. MCC relies on the integrated action of three components: 1) mucus secretion by goblet cells and submucosal glands; 2) the movement of cilia on epithelial cells which propels the mucus across the luminal surface; and 3) ion transport into and out of luminal epithelial cells which concomitantly controls the flow of water into the mucus.

It is now known that nucleoside phosphates such as uridine 5'-triphosphate (UTP) modulate all of the components of the MCC system. First, UTP has been shown to increase both the rate and total amount of mucin secretion by goblet cells in vitro (M. Lethem, et al., *Am J. Respir. Cell Mol. Biol.* 9, 315–22 (1993)). Second, UTP has been shown to increase cilia beat frequency in human airway epithelial cells in vitro (D. Drutz, et al., *Drug Dev. Res.* 37(3), 185 (1996)). And third, UTP has been shown to increase Cl$^-$ secretion, and hence, water secretion from airway epithelial cells in vitro (S. Mason, et al., *Br. J. Pharmacol.* 103, 1649–56 (1991)). In addition, it is thought that the release of surfactant from Type II alveolar cells in response to UTP (Gobran, *Am. J. Physiol.* 267, L625–L633 (1994)) contributes to optimal functioning of the lungs and may assist in maximizing MCC (M. Knowles, et al., *N. Engl. J. Med.* 325, 533–38 (1991)). UTP has been shown to increase intracellular Ca$^{++}$ due to stimulation of phospholipase C by the P2Y$_2$ receptor (H. Brown, et al., *Mol. Pharmocol.* 40, 648–55 (1991)).

UTP's modulation of all components of the mucociliary escalator system results in a 2.5-fold improvement in lung mucociliary clearance in normal volunteers without any significant side-effects (K. Olivier, et al., *Am J. Respir. Crit. Care Med.* 154, 217–23 (1996)). In addition, UTP significantly enhanced cough clearance (clearance of retained secretions by coughing) in patients with PCD (P. Noone, et al., *Am. J. Respir. Crit. Care Med.* 153, A530 (1996)).

Because of UTP's demonstrated ability to increase the clearance of retained mucous secretions, applicants were motivated to investigate whether other nucleoside phosphates could be equally, if not more, effective in clearing retained mucous secretions. The present invention is based upon this investigation.

Dinucleotides in the prior art are listed in Table I, along with their corresponding references.

TABLE I

DINUCLEOTIDES IN THE LITERATURE
(numbers in parentheses correspond to references that follow)

| Np$_2$N | Np$_2$N' | Np$_3$N | Np$_3$N' | Np$_4$N | Np$_4$N' |
|---|---|---|---|---|---|
| Ap$_2$A (4,1) | Ap$_2$NAD (6) | Up$_3$U (1) | Ap$_3$T (20) | Up$_4$U (2,3) | Ap$_4$U (3) |
| Gp$_2$G (5,1) | Ap$_2$TAD (6) | Ap$_3$A (1,4,29) | m$^7$Gp$_3$G (5) | Ap$_4$A (1,4,29) | Ap$_4$C (3) |
| m$^7$Gp$_2$m$^7$G (5) | Ap$_2$C-NAD (6) | Xp$_3$X (1) | m$^{2,2,7}$Gp$_3$G (5) | Cp$_4$C (3) | Ap$_4$9 (3) |
| | Ap$_2$C-PAD (6) | m$^7$Gp$_3$m$^7$G (5) | m$^{2,7}$Gp$_3$G (5) | Gp$_4$G (1,5) | Gp$_4$U (3) |
| | Ap$_2$BAD (6) | Gp$_3$G (1) | | Xp$_4$X (1) | Gp$_4$C (3) |
| | m$^7$Gp$_2$G (5) | | | Dp$_4$D (15) | Up$_4$C (3) |
| | Up$_2$U (43) | | | eAp$_4$eA (7) | Ap$_4$T (20) |
| | | | | m$^7$Gp$_4$m$^7$G (5) | m$^7$Gp$_4$G (5) |
| | | | | | m$^{2,7}$Gp$_4$G (5) |
| | | | | | m$^{2,2,7}$Gp$_4$G (5) |

| Np$_5$N | Np$_5$N' | Np$_6$N | Np$_6$N' | Np$_8$N |
|---|---|---|---|---|
| Ap$_5$A (4) | Ap$_5$T (20) | Ap$_6$A (4) | Ap$_6$T (20) | Ap$_8$A (4) |

TABLE I-continued

DINUCLEOTIDES IN THE LITERATURE
(numbers in parentheses correspond to references that follow)

| AppZppA Z | DppZppD Z | ApZppZpA Z | ApSpZpSpA Z |
|---|---|---|---|
| $CH_2$ (8) | $CH_2$ (15) | $CH_2$ (8) | CHF (8) |
| $CH_2CH_2$ (8) | $CH_2CH_2$ (15) | $CH_2CH_2$ (8) | $CF_2$ (8) |
| CHF (8) | CHF (15) | CHF (8) | O (8) |
| $CF_2$ (8) | $CF_2$ (15) | $CF_2$ (8) | |
| CHCl (8) | CHCl (15) | CHCl (8) | |
| $CCl_2$ (8) | $CCl_2$ (15) | $CCl_2$ (8) | |

A = Adenosine
U = Uridine
G = Guanosine
T = Thymidine
X = Xanthosine
TAD = Tiazofurin
BAD = Benzamide riboside
D = 2,6-Diaminopurine
eA = Ethenoadenosine
$m^7G$ = 7-Methylguanosine
$m^{2,7}G$ = 2,7-Dimethylguanosine
$m^{2,2,7}G$ = 2,2,7-Trimethylguanosine
NAD = nicotinamide riboside
C-NAD = C-nicotinamide riboside
C-PAD = C-picolinamide riboside
N = Nucleoside
(1) M. A. G. Sillero et al., Eur. J. Biochem., 76, 331 (1977)
(2) C. G. Vallejo et al., Biochim. Biophys. Acta, 483, 304 (1976)
(3) H. Coste et al., J. Biol. Chem., 262, 12096 (1987)
(4) K. E. Ng et al., Nucleic Acid Res., 15, 3573 (1987)
(5) J. Stepinski et al., Nucleosides & Nucleotides, 14, 717 (1995)
(6) A. Zatorski et al., J. Med. Chem., 39, 2422 (1996)
(7) P. Rotilan et al., FEBS, 280, 371 (1991)
(8) P. C. Zamecnik et al., Proc. Natl. Acad. Sci., 89, 2370 (1992)
(9) J. Walker et al., Biochemistry, 32, 14009 (1993)
(10) R. H. Hiderman et al., J. Biol. Chem., 266, 6915 (1991)
(11) J. Luthje et al., Eur. J. Biochem., 173, 241 (1988)
(12) R. H. Silverman et al., Microbiological Rev., 43, 27 (1979)
(13) C. D. Lobaton et al., Eur. J. Biochem., 50, 495 (1975)
(14) G. Lowe et al., Nucleosides & Nucleotides, 10, 181 (1991)
(15) G. M. Blackburn et al., Nucleosides & Nucleotides, 10, 549 (1991)
(16) J. C. Baker et al., Mutation Res., 208, 87 (1988)
(17) G. Klein et al., Biochemistry, 27, 1897 (1988)
(18) E. Castro et al., Br. J. Pharmacol., 100, 360 (1990)
(19) D. R. Elmaleh et al., Proc. Natl. Acad. Sci., 81, 918 (1984)
(20) R. Bone et al., J. Biol. Chem., 261, 16410 (1986)
(21) Fed. Amer. Soc. Exper. Bio., Abstr. Part I, no. 1878 (1991)
(22) M. T. Miras-Portugal et al., Ann. NY Acad. Sci., 603, 523 (1990)
(23) A. Guranowski et al., Biochemistry, 27, 2959 (1988)
(24) F. Grummt et al., Plant Mol. Bio., 2, 41 (1983)
(25) A. G. McLennan et al., Nucleic Acid Res., 12, 1609 (1984)
(26) P. Zamecnik et al., Analytical Biochem., 134, 1 (1983)
(27) E. Rapaport et al., Proc. Natl. Acad. Sci., 78, 838 (1981)
(28) T. Kimura et al., Biol. Pharm. Bull., 18, 1556 (1995)
(29) E. Schulze-Lohoff et al., Hypertension, 26, 899 (1995)
(30) B. K. Kim et al., Proc. Natl. Acad. Sci., 89, 11056 (1992)
(31) P. C. Zamecnik et al., Proc. Natl. Acad. Sci., 89, 2370 (1992)
(32) H. Morii et al., Eur. J. Biochem., 205, 979 (1992)
(33) E. Castro et al., Pflugers Arch., 426, 524 (1994)
(34) H. Schluter et al., Nature, 367, 186 (1994)
(35) E. Castro et al., Br. J. Pharmacol., 206, 833 (1992)
(36) T. Casillas et al., Biochemistry, 32, 14203 (1993)
(37) J. Pintor et al., J. Neurochem., 64, 670 (1995)
(38) E. Castro et al., J. Biol. chem., 270, 5098 (1995)
(39) V. A. Panchenko et al., Neuroscience, 70, 353 (1996)
(40) E. Castro et al., Br. J. Pharmacol., 100, 360 (1990)
(41) J. Pintor et al., Gen. Pharmac., 26, 229 (1995)
(42) J. Pintor et al., Br. J. Phamacol., 115, 895 (1995)
(43) A. Kanavarioti al., Tett. Lett., 32, 6065 (1991)

SUMMARY OF THE INVENTION

The invention provides novel pharmaceutical compositions comprising compounds of Formula I. The invention also provides compounds useful in the clearance of retained mucous secretion and the enhancement of ciliary beat frequency. Accordingly, a broad embodiment of the invention is directed to compounds of general Formula I or the pharmaceutically acceptable non-toxic salts thereof:

Formula I

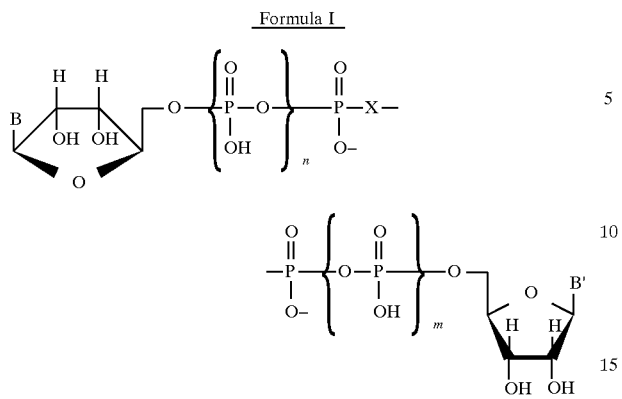

wherein:
X is oxygen, methylene, difluoromethylene, imido;
n=0 or 1;
m=0 or 1;
n+m=0, 1 or 2; and B and B' are each independently a purine residue or a pyrimidine residue linked through the 9- or 1-position, respectively. In the instance where B and B' are uracil, attached at N−1 position to the ribosyl moiety, then the total of m+n may equal 3 or 4 when X is oxygen (see example 1). The ribosyl moieties are in the D- configuration, as shown, but may be L-, or D- and L-. The D- configuration is preferred.

The compounds of the present invention are highly selective agonists of the $P2Y_2$ purinergic receptor, thus, they may be useful in the treatment of chronic obstructive pulmonary diseases such as chronic bronchitis, PCD, and cystic fibrosis, and may also be useful in the treatment of immobilized patients who are at risk for developing pneumonia. Furthermore, because of their general ability to clear retained mucus secretions and stimulate ciliary beat frequency, the compounds of the present invention may also be useful in the treatment of sinusitis and otitis media. Additionally, it is postulated that the compounds of the present inventions could enhance the performance of athletes by increasing the clearance of mucous secretions from the lungs.

DETAILED DESCRIPTION OF THE INVENTION

This invention provides novel pharmaceutical compositions comprising compounds of Formula I. The invention also provides compounds useful in the clearance of retained mucous secretion and the enhancement of ciliary beat frequency. Accordingly, a broad embodiment of the invention is directed to compounds of general Formula I or the pharmaceutically acceptable non-toxic salts thereof:

Formula I

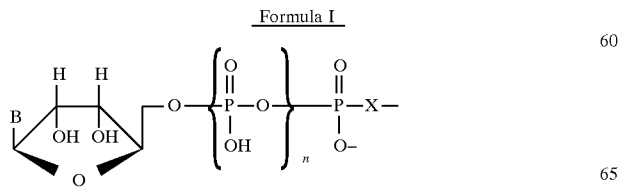

-continued
Formula I

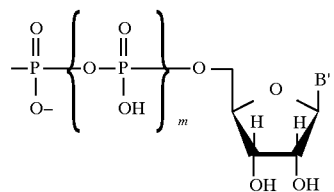

wherein:
X is oxygen, methylene, difluoromethylene or imido;
n=0 or 1;
m=0 or 1;
n+m=0, 1 or 2; and B and B' are each independently a purine residue, as in Formula II, or a pyrimidine residue, as in Formula m, linked through the 9- or 1-position, respectively. In the instance where B and B' are uradl, attached at N−1 position to the ribosyl moiety, then the total of m+n may equal 3 or 4 when X is oxygen (see example 1). The ribosyl moieties are in the D-configuration, as shown, but may be L-, or D- and L-. The D- configuration is preferred.

Formula II

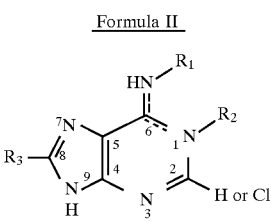

The substituted derivatives of adenine include adenine 1-oxide; 1,N6-(4- or 5- substituted etheno) adenine; 6-substituted adenine; or 8-substituted aminoadenine, where R' of the 6- or 8-HNR' groups are chosen from among: arylalkyl ($C_{1-6}$) groups with the aryl moiety optionally functionalized as described below; alkyl; and alkyl groups with functional groups therein, such as: ([6-aminohexyl] carbamoylmethyl)-, and ω-acylated-amino(hydroxy, thiol and carboxy)alkyl($C_{2-10}$)- and their ω-acylated-amino (hydroxy, thiol and carboxy) derivatives where the acyl group is chosen from among, but not limited to, acetyl, trifluroroacetyl, benzoyl, substituted-benzoyl, etc., or the carboxylic moiety is present as its ester or amide derivative, for example, the ethyl or methyl ester or its methyl, ethyl or benzamido derivative. The ω-amino(hydroxy, thiol) moiety may be alkylated with a $C_{1-4}$ alkyl group.

Likewise, B or B', or both may be a pyrimidine with the general formula of FIG. III, linked through the 1-position:

Formula III

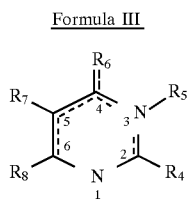

wherein:
$R_4$ is hydrogen, hydroxy, mercapto, amino, cyano, aralkoxy, $C_{1-6}$ alkylthio, $C_{1-6}$ alkoxy, $C_{1-6}$ alkylamino and dialkylamino, the alkyl groups optionally linked to form a heterocycle;

$R_5$ is hydrogen, acyl, $C_{1-6}$ alkyl aroyl, $C_{1-5}$ alkanoyl, benzoyl, or sulphonate;

$R_6$ is hydroxy, mercapto, alkoxy, aralkoxy, $C_{1-6}$-alkylthio, $C_{1-5}$ disubstituted amino, triazolyl, alkylamino or dialkylamino, where the alkyl groups are optionally linked to form a heterocycle or link to $N^3$ to form an optionally substituted ring;

$R_7$ is hydrogen, hydroxy, cyano, nitro, alkenyl, with the alkenyl moiety optionally linked through oxygen to form a ring optionally substituted on the carbon adjacent to the oxygen with alkyl or aryl groups, substituted alkynyl or hydrogen where $R_7$ is amino or substituted amino and halogen, alkyl, substituted alkyl, perhalomethyl (e.g., $CF_3$), $C_{2-6}$ alkyl, $C_{2-3}$ alkenyl, or substituted ethenyl (e.g., allylamino, bromvinyl and ethyl propenoate, or propenoic acid), $C_{2-3}$ alkynyl or substituted alkynyl and together $R_6$-$R_5$ may form a 5 or 6-membered saturated or unsaturated ring bonded through N or O at $R_6$, such a ring may contain substituents that themselves contain functionalities;

$R_8$ is hydrogen, alkoxy, arylalkoxy, alkylthio, arylalkylthio, carboxamidomethyl, carboxymethyl, methoxy, methylthio, phenoxy or phenylthio.

In the general structure of Formula III above, the dotted lines in the 2- to 6- positions are intended to indicate the presence of single or double bonds in these positions; the relative positions of the double or single bonds being determined by whether the $R_4$, $R_5$ and $R_6$ substituents are capable of keto-enol tautomerism.

In the general structures of Formula II and III above, the acyl groups advantageously comprise alkanoyl or aroyl groups. The alkyl groups advantageously contain 1 to 8 carbon atoms, particularly 1 to 4 carbon atoms optionally substituted by one or more appropriate substituents, as described below. The aryl groups including the aryl moieties of such groups as aryloxy are preferably phenyl groups optionally substituted by one or more appropriate substituents, as described below. The above mentioned alkenyl and alkynyl groups advantageously contain 2 to 8 carbon atoms, particularly 2 to 6 carbon atoms, e.g., ethenyl or ethynyl, optionally substituted by one or more appropriate substituents as described below.

Appropriate substituents on the above-mentioned alkyl, alkenyl, alkynyl, and aryl groups are advantageously selected from halogen, hydroxy, $C_{1-4}$ alkoxy, $C_{1-4}$ alkyl, $C_{6-12}$ aryl, $C_{6-12}$ arylalkoxy, carboxy, cyano, nitro, sulfonamido, sulfonate, phosphate, sulfonic, amino and substituted amino wherein the amino is singly or doubly substituted by a $C_{1-4}$ alkyl, and when doubly substituted, the alkyl groups optionally being linked to form a heterocycle.

The compounds of the present invention also encompass their non-toxic pharmaceutically acceptable salts, such as, but not limited to, an alkali metal salt such as sodium or potassium; an alkaline earth metal salt such as manganese, magnesium or calcium; or an ammonium or tetraalkyl ammonium salt, i.e., $NX_4^+$ (wherein X is $C_{1-4}$). Pharmaceutically acceptable salts are salts that retain the desired biological activity of the parent compound and do not impart undesired toxicological effects. The present invention also encompasses the acylated prodrugs of the compounds disclosed herein. Those skilled in the art will recognize various synthetic methodologies which may be employed to prepare non-toxic pharmaceutically acceptable salts and acylated prodrugs of the compounds encompassed by Formula I.

The pharmaceutical utility of compounds of this invention are indicated by the inositol phosphate assay for $P2Y_2$ activity. This widely used assay, as described in E. Lazarowski, et al., *Brit. J. Pharm.* 116, 1619–27 (1995), relies on the measurement of inositol phosphate formation as a measurement of activity of compounds activating receptors linked via G-proteins to phospholipase C.

The compounds of general Formula I may be administered orally, topically, parenterally, by inhalation or spray, intra-operatively, rectally, or vaginally in dosage unit formulations containing conventional non-toxic pharmaceutically acceptable carriers, adjuvants and vehicles. The term topically as used herein includes patches, gels, creams, ointments, or nose, ear or eye drops. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general Formula I may be present in association with one or more non-toxic pharmaceutically acceptable carriers or diluents or adjuvants and, if desired, other active ingredients. One such carrier would be sugars, where the compounds may be intimately incorporated in the matrix through classification or simply admixed with the carrier (e.g., lactose, sucrose, trehalose, mannitol) or other acceptable excipients for lung or airway delivery.

The pharmaceutical compositions containing compounds of general Formula I may be in a form suitable for oral use, for example, as tablets, lozenges, aqueous or oily suspensions, dispersible powders or granules, emulsion, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Aqueous suspensions contain the active materials in admixture with excipients suitable for the manufacture of aqueous suspensions. Such excipients are suspending agents, for example: sodium carboxymethylcellulose, methylcellulose and sodium alginate. Dispersing or wetting agents may be a naturally-occurring phosphatide or condensation products of an allylene oxide with fatty acids, or condensation products of ethylene oxide with long chain aliphatic alcohols, or condensation products of ethylene oxide with partial esters from fatty acids and a hexitol, or condensation products of ethylene oxide with partial esters derived from fatty acids and hexitol anydrides. Those skilled in the art will recognize the many specific excipients and wetting agents encompassed by the general description above. The aqueous suspensions may also contain one or more preservatives, for example, ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, may also be present.

Compounds of general Formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle. The sterile injectable preparation may be a sterile injectable solution or suspension in a non-toxic parentally acceptable diluent or solvent. Among the acceptable vehicles and solvents that may be employed are sterile water, saline solution, or Ringer's solution.

The compounds of general Formula I may also be administered in the form of suppositories for ear, rectal or vaginal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order of from about $10^{-7}$M to about $10^{-1}$M are useful in the treatment of the above-indicated conditions. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be apparent to those skilled in the art of organic synthesis as well as the conditions necessary to attach and remove such groups.

The invention is illustrated further by the following examples which are not to be construed as limiting the invention in scope or spirit to the specific procedures described in them.

EXAMPLE 1

Preparation of $P^1,P^4$-Di(uridine 5'-$P^2,P^3$-methylenetetraphosphate)

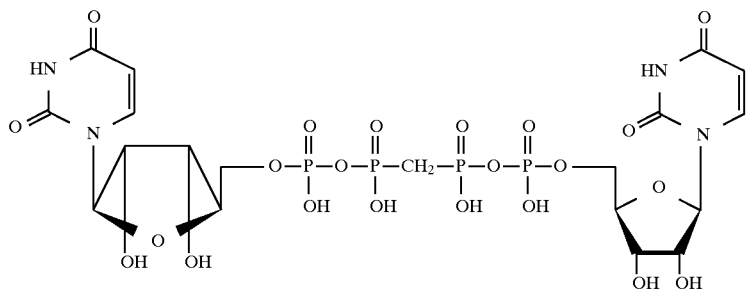

Methylenediphosphonic acid (0.0088 g, 0.05 mmol) was dissolved in anhydrous DMF (0.5 mL) with the addition of tributylamine (24 µL, 0.1 nmol). The solution was evaporated to dryness twice with anhydrous DMF (2×1 mL), the dried residue dissolved in anhydrous DMF (0.5 mL), and a solution of similarly-dried uridine 5'-monophosphomorpholidate 4-morpholine-N,N'-dicyclohexylcarboxamidine salt (0.137 g, 0.2 mmol) in anhydrous DMF (0.5 mL) added. The reaction mixture was heated at 80°–90° C. for 7 h, then the solvent was removed by evaporation under reduced pressure. The residue was dissolved in water (2 mL) and applied to a column of DEAE cellulose (2.5×50 cm bed volume) in the bicarbonate form. The column was eluted with water, followed by a gradient of ammonium bicarbonate (0–0.33M, in 900 mL). The progress of the elution was followed by monitoring absorbance of the eluate at 254 nm; the fraction eluting between 0.23 and 0.26M was collected, evaporated to dryness and desalted by repeated evaporation with deionized water. The residue was dissolved in water (300 µL) and purified in 50 µL aliquots by semipreparative HPLC (Alltech PEI 5µ, 10×250 mm, gradient 0–0.66-M ammonium bicarbonate, 5.0 mL/min, 20 min); peaks eluting at 8.7–9.0 min from each run were combined and lyophilized to yield the title compound (0.007 mmol, 14% yield, quantitated by comparison of its absorbance at $\lambda_{max}$ 263 with that of a standard solution of uridine monophosphate). Chromatographic purity was 96.5% on an Alltech PEI column, gradient 0–0.66-M ammonium bicarbonate, 1.0 mL/min, 20 min., retention time 13.03 min. $^1$H NMR in $D_2O$ (δ ppm from tetramethylsilane): 2.39, (t, J=21.5 Hz, 2H); 4.12 (m, 6H); 4.243 (m, 4H); 5.841 (d, J=7.9 Hz, 2H); 5.847 (d, J=4.5 Hz, 2H); 7.77, d, J=8.1 Hz, 2H). $^{31}$P NMR in $D_2O$ (ppm from $H_3PO_4$) −10.2 to −10.7 (complex m, 2P); 7.8 to 8.4 (complex m, 2P).

EXAMPLE 2

Preparation of $P^1,P^4$-Di(uridine 5'-$P^2,P^3$-difluoromethylenetetraphosphate)

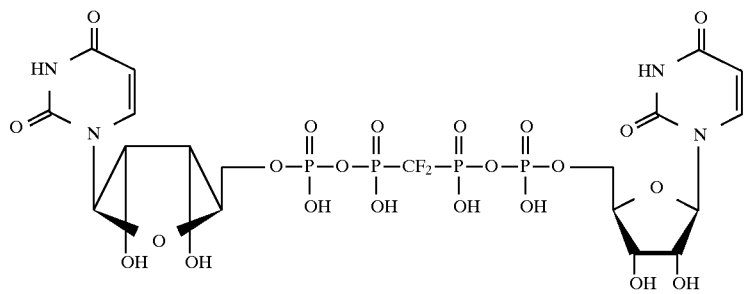

The tributylammonium salt of difluoromethylenediphosphonic acid (as described in C. McKenna, et al., *J. Org. Chem.* 46, 4574–76 (1981) and D. Burton, et al., *J. Fluorine Chem.* 15, 263–66 (1980)) (0.014 g, 0.025 mmol), converted to the salt as described for methylenephosphonic acid was dissolved in a solution of uridine 5'-monophosphomorpholidate 4-morpholine-N,N'-dicyclohexylcarboxamidine salt (0.034 g, 0.05 mmol) in anhydrous dimethyl sulfoxide (0.7 mL), and heated for 9 days at 50° C. The cooled reaction mixture was diluted with water and applied to a column of DEAE cellulose (2.5×50 cm bed volume) in the bicarbonate form. The column was eluted with water, followed by a gradient of ammonium bicarbonate (0–0.33M, total volume 900 mL). The progress of the elution was followed by monitoring absorbance of the eluate at 254 nm. The fraction eluting between 0.29 and 0.30M was evaporated to dryness and desalted by repeated evaporations with deionized water to yield the title compound (0.0011 mmol, 4.4% yield, quantitated by comparison of its absorbance at $\lambda_{max}$ 263 nm with that of a standard solution of uridine monophosphate). Chromatographic purity was 88.5% on an Alltech PEI column, gradient 0–0.66-M ammonium bicarbonate, 1.0 mL/min, 20 min., retention time 12.03 min. $^1$H NMR in $D_2O$ (δ ppm from tetramethylsilane): 4.05–4.085 (m, 6H); 4.18–4.20 (m, 4H); 5.80 (d, J=8.0 Hz, 2H); 5.81 (d, J=4.5 Hz, 2H); 7.77 (d, J=7.9 Hz, 2H). $^{31}$P NMR in $D_2O$ (ppm from $H_3PO_4$) –10.63 (dd, J=18.3, 11.3 Hz, 2P); –5.83 (tdd, J=75, 18.3, 11.3 Hz, 2P). $^{19}$F NMR in $D_2O$: 73.406 (t, J=75.5 Hz).

Similar treatment of uridine 5'-monophosphomorpholidate 4-morpholine-N,N'-dicyclohexylcarboxamidine salt (0.068 g, 0.1 mmol) with tetrabutylammonium imidodiphosphate 0.05 mmol) in anhydrous DMF (1.0 mL) for 20 days at room temperature yielded the title compound as the ammonium salt (1.6%). $^1$H NMR in $D_2O$ (δ ppm from tetramethylsilane): 4.07–4.09 (m, 6H); 4.17–4.22 (m, 4H); 5.79 (d, J=8.1 Hz, 2H); 5.80 (d, J=4.8 Hz, 2H); 7.78, d, J=8.2 Hz, 2H). $^{31}$P NMR in $D_2O$ (ppm from $H_3PO_4$) –10.82 (m, 4P); P—P coupling pattern similar that of $P^1,P^4$-di(adenosine 5'-tetraphosphate (Sigma) run under same conditions.

EXAMPLE 3

Preparation of $P^1,P^4$-Di(uridine 5'-$P^2,P^3$-imidotetraphosphate)

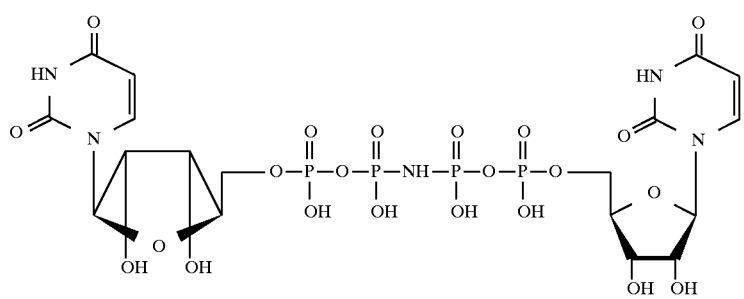

EXAMPLE 4

Preparation of $P^1,P^4$-Di(4-thiouridine 5'-tetraphosphate)

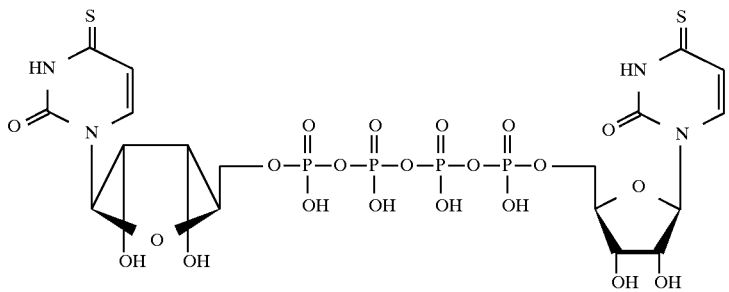

4-Thiouridine 5'-diphosphate (Sigma, ammonium salt, 24.49 mg, 0.05 mmol), converted to the tributylammonium salt as described for 4-thiouridine monophosphate (above), was dissolved in anhydrous DMF (0.5 mL) and carbonyldiimidazole (4.86 mg, 0.03 mmol) was added. The reaction mixture was set aside under nitrogen at room temperature for twelve days. The reaction mixture was evaporated to dryness under vacuum at room temperature, the residue dissolved in water (2 mL), and applied to a column of DEAE cellulose (2.5×50 cm bed volume) in the bicarbonate form. The column was eluted with water (~250 mL), then with a gradient of ammonium bicarbonate (0–0.33M, total volume 900 mL). This was followed by a gradient of 0.33 to 0.5M ammonium bicarbonate over 400 mL. The progress of the elution was followed by monitoring absorbance of eluate at 280 nm. The fraction eluting between 0.336 and 0.339M was evaporated to dryness and desalted by repeated evaporations with deionized water to yield the title compound (0.0045 mmol, 18% yield, quantitated by comparison of its absorbance at $\lambda_{max}$ 332 nm with that of a standard solution of 4-thiouridine diphosphate). $^1$H NMR in $D_2O$ (δ ppm from tetramethylsilane): 4.09–4.11 (m, 6H); 4.18–4.24 (m, 4H); 5.76 (d, J=4.5 Hz, 2H); 6.47 (d, J=7.7 Hz, 2H); 7.67, d, J=8.2 Hz, 2H). $^{31}$P NMR in $D_2O$ (ppm) from $H_3PO_4$) −22.57 to −22.73 (m, 2P); −10.76 to −10.91 (m, 2P); P—P coupling pattern similar to that of $P^1,P^4$-di(adenosine 5'-tetraphosphate (Sigma) run under same conditions.

A 100 ml round bottomed flask was charged with a DMF solution of uridine 5'-diphosphate tributylammonium salt (1.81 mmol, 10 ml) and carbonyldiimidazole (469 mg, 2.90 mmol) and the solution was stirred under $N_2$ for 2 hours. To this was added a DMF solution of uridine 5'-triphosphate tributylammonium salt (1.81 mmol, 10 ml) and the solution was stirred at 60° C. for 24 hours. The solution was evaporated in vacuo and purified two times by column chromatography (DEAE Sephadex; $H_2O>0.5M$ $NH_4HCO_3$ gradient). The pure fractions were concentrated in vacuo at 35° C., and $H_2O$ added and reevaporated ten times to obtain a white solid (200 mg). $^1$H NMR ($D_2O$, TMS) δ 4.0 (m, br, 6H), 4.1 (m, 4H), 5.7 (m, 4H), 7.7 (d, J=8.1 Hz, 2H); $^{31}$P NMR ($D_2O$, $H_3PO_4$ std) δ −22.3 (m, 3P), −10.6 (d, J=42.9 Hz, 2P).

EXAMPLE 5

Preparation of $P^1,P^5$-Di(uridine 5'-pentaphosphate)

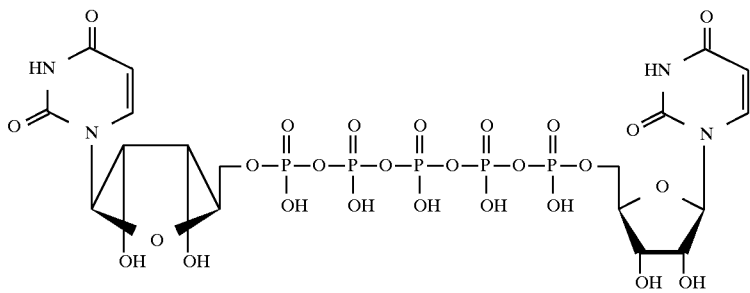

EXAMPLE 6

Preparation of P[1],P[4]-Di(3,N[4]-ethenocytidine 5'-tetraphosphate)

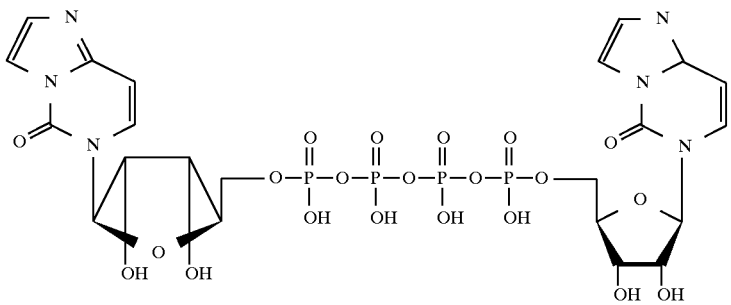

To a solution of P[1],P[4]-di(cytidine 5'-tetraphosphate) (3, Table I; ammonium salt, 6 μmol in 0.66 mL water) was added sodium bicarbonate (0.005 g, 60 μmol) and the solution was lyophilized to remove ammonia. The residue was dissolved in a mixture of water and (0.20 mL) and chloroacetaldehyde solution (50% in water, 0.30 mL), and the reaction mixture set aside at room temperature for six days. The reaction mixture was lyophilized, and the gummy residue partitioned between deuterium oxide (0.7 mL) and methylene chloride (1.5 mL). The $^1$H NMR spectrum of the aqueous solution indicated that the ethenylation had progressed about 50%, while the $^{31}$P spectrum confirmed that the tetraphosphate chain remained intact. Additional chloroacetaldehyde solution (0.25 mL) was added to the NMR solution and the mixture set aside for a further ten days. The solution was lyophilized, and the residue lyophilized again with deuterium oxide to remove exchangeable protons. The residue was partitioned between deuterium oxide and methylene chloride as before, and complete conversion to the ethenyl derivative confirmed by NMR spectroscopy. The deuterium oxide solution was applied to a column of DEAE cellulose (2.5×30 cm bed volume) in the bicarbonate form. The column was eluted with water (~250 mL), followed by a gradient of 0 to 0.5M ammonium bicarbonate over 1000 mL. The progress of the elution was followed by monitoring absorbance of the eluate at 280 nm. The fraction eluting between 0.29 and 0.32M was evaporated to dryness and desalted by repeated evaporations with deionized water to yield the title compound (1.584 μmol, 26.4% yield, quantitated by comparison of its absorbance at $\lambda_{max}$ 273 nm with that of a standard solution of 3,N[4]-ethenocytidine 5'-monophosphate). $^1$H NMR in D$_2$O (δ ppm from tetramethylsilane): 4.123 (m, 6H); 4.258 (m, 4H); 5.986 (s, 2H); 6.92 (d, J=8.1 Hz, 2H); 7.461 (s, 2H); 7.772 (s, 2H); 8.00 (d, J=7.6 Hz, 2H). $^{31}$P NMR in D$_2$O (ppm from H$_3$PO$_4$) −22.474 (m, 2P); −10.650 (m, 2P); P—P coupling pattern closely similar to that of P[1],P[4]-di(adenosine 5'-tetraphosphate [Sigma]) run under same conditions.

EXAMPLE 7

Pharmacological activity as measured by the inositol phosphate assay

The compounds of Examples 1–6 were tested for their ability to elicit P2Y$_1$, P2Y$_2$, P2Y$_4$ and P2Y$_6$ receptor activity using the inositol phosphate assay as described by E. Lazarowski, et al., *Brit. J. Pharm.* 116, 1619–27 (1995). The results are summarized in Table II below.

TABLE II

DINUCLEOTIDE ACTIVITY SUMMARY
EC50's (μmol)

| Example | P2Y1 | P2Y2 | P2Y4 | P2Y6 |
|---------|------|------|------|------|
| 1 | IA | WEAK | 11.1 (60%) | IA |
| 2 | IA | 5.71 | 1.0 (80%) | WEAK |
| 3 | 3.67 | 0.63 | 1.19 | 2.56 |
| 4 | IA | 0.02 | n/a | 0.05 (20%) |
| 5 | 31.2 (55%) | 3.8 (80%) | 2.87 | 92.64 |
| 6 | WEAK | 0.46 | 19.8 (75%) | IA |

IA  Response <2-fold basal
WEAK  EC50 > 100 μmol
(XX%)  Percentage response of same study positive control The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of general Formula I:

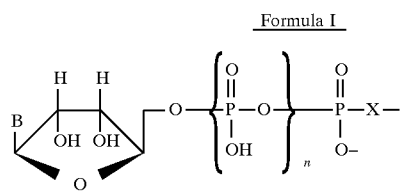

Formula I

-continued

Formula I

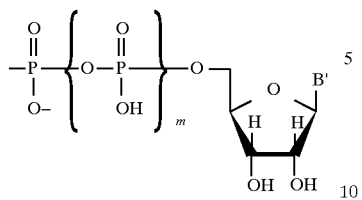

or the pharmaceutically acceptable non-toxic salts thereof wherein:

X is oxygen methylene, difluoromethylene or imido;

n=0 or 1 or 2;

m=0 or 1 or 2;

the total number of phosphate groups is between 2 and 6; and

B and B' are each independently a purine residue, as in Formula II, or a pyrimidine residue, as in Formula III, linked through the 9- or 1- position respectively:

Formula II

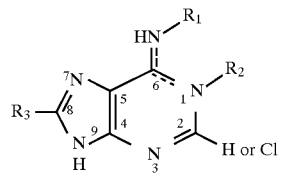

wherein:

$R_2$ is O or is absent; or $R_1$ and $R_2$ taken together may form optionally substituted 5-membered raised imidazole ring, or $R_1$ of the 6-HNR$_1$ group or $R_3$ of the 8-HNR$_3$ group is chosen from the group consisting of:
(a) arylalkyl ($C_{1-6}$) groups with the aryl moiety optionally substituted,
(b) alkyl,
(c) ([6-aminohexyl]carbamoylmethyl),
(d) ω-amino alkyl ($C_{2-10}$),
(e) ω-hydroxy alkyl ($C_{2-10}$),
(f) ω-thiol alkyl ($C_{2-10}$),
(g) ω-carboxy alkyl ($C_{2-10}$),
(h) the ω-acylated derivatives of (b), (c) or (d) wherein the acyl group is either acetyl, trifluroroacetyl, benzoyl, or substituted-benzoyl alkyl ($C_{2-10}$), and
(i) ω-carboxy alkyl ($C_{2-10}$) as in (e) above wherein the carboxylic moiety is an ester or an amide;

Formula III

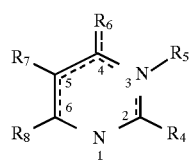

wherein:

$R_4$ is hydroxy, mercapto, amino, cyano, aralkoxy, $C_{1-6}$ alkylthio, $C_{1-6}$ alkoxy, $C_{1-6}$ alkylamino or dialkylamino, wherein the alkyl groups of said dialkylamino are optionally linked to form a heterocycle;

$R_5$ is hydrogen, acyl, $C_{1-6}$ alkyl, aroyl $C_{1-5}$ alkanoyl, benzoyl, or sulphonate, $R_6$ is hydroxy, mercapto, alkoxy, aralkoxy, $C_{1-6}$-alkylthio, $C_{1-5}$ disubstituted amino, triazolyl, alkylamino or diamino, wherein the alkyl groups of said dialkylamino are optionally linked to form a heterocycle or linked to $N^3$ to form am optionally substituted ring;

$R_5$–$R_6$ together forms a 5 or 6-membered saturated or unsaturated ring bonded through N or O at $R_6$, wherein said ring is optionally substituted;

$R_7$ is selected from the group consisting of:
(a) hydrogen,
(b) hydroxy,
(c) cyano,
(d) nitro,
(e) alkenyl, wherein the alkenyl moiety is optionally linked through oxygen to form a ring optionally substituted with alkyl or aryl groups on the carbon adjacent to the oxygen,
(f) substituted alkynyl
(g) hydrogen
(h) halogen,
(i) alkyl,
(j) substituted alkyl,
(k) perhalomethyl,
(l) $C_{2-6}$ alkyl,
(m) $C_{2-3}$ alkenyl,
(n) substituted ethenyl,
(o) $C_{2-3}$ alkynyl and
(p) substituted alkynyl when $R_6$ is other than amino or substituted amino;

$R_8$ is selected from the group consisting of:
(a) hydrogen,
(b) alkoxy,
(c) arylalkoxy,
(d) alkylthio,
(e) arylalkylthio,
(f) carboxamidomethyl,
(g) carboxymethyl,
(h) methoxy,
(i) methylthio,
(j) phenoxy and
(k) phenylthio.

2. A compound according to claim 1, where the acyl groups of Formulas II and III are alkyl acyl groups which have 2 to 5 carbon atoms, or aryl acyl groups wherein both the alkyl and aryl moieties of said acyl groups are optionally substituted with substituents selected from the group consisting of halogen, hydroxy, $C_{1-4}$ alkoxy, $C_{1-4}$ alkyl, $C_{6-12}$ aryl, $C_{6-12}$ arylalkoxy, carboxy, cyano, nitro, sulfonamido, sulfonate, phosphate, sulfonic, amino and substituted amino wherein the amino is singly or doubly substituted by a $C_{1-4}$ alkyl, and when doubly substituted, the alkyl groups are linked to form a heterocycle.

3. A compound according to claim 1, wherein B and B' are uracil attached at the N–1 position to the ribosyl moiety, and wherein the total number of phosphates is between 2 and 4 when X is not oxygen, and either 5 or 6 when X is oxygen.

4. $P^1,P^4$-Di(uridine 5'-$P^2,P^3$-methylenetetraphosphate).

5. $P^1,P^4$-Di(uridine 5'-$P^2,P^3$-difluoromethylenetetraphosphate).

6. $P^1,P^4$-Di(uridine 5'-$P^2,P^3$-imidotetraphosphate).

7. $P^1,P^4$-Di(4-thiouridine 5'-tetraphosphate).

8. $P^1,P^5$-Di(uridine 5'-pentaphosphate).

9. $P^1,P^4$-Di(3,$N^4$-ethenocytidine 5'-tetraphosphate).

* * * * *

Disclaimer 5,837,861—William Pendergast, Durham; Benjamin R. Yerxa, Raleigh; Janet L. Rideout, Raleigh; Suhaib M. Siddiqi, Raleigh all of N.C. DINUCLEOTIDES AND THEIR USE AS MODULATORS OF MUCOCILIARY CLEARANCE AND CILIARY BEAT FREQUENCY. Patent dated November 17, 1998. Disclaimer filed March 28, 2001, by the assignee, Inspire Pharmaceuticals, Inc.

Hereby enters this disclaimer to claims 1 and 2 of said patent.

*(Official Gazette, June 5, 2001)*